(12) United States Patent
Yamasaki (10) Patent No.: US 11,360,069 B2
(45) Date of Patent: Jun. 14, 2022

(54) INSPECTION APPARATUS AND INSPECTION SYSTEM

(71) Applicant: KYOCERA Corporation, Kyoto (JP)

(72) Inventor: Hirohide Yamasaki, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 255 days.

(21) Appl. No.: 16/073,356

(22) PCT Filed: Jan. 16, 2017

(86) PCT No.: PCT/JP2017/001243
§ 371 (c)(1),
(2) Date: Jul. 27, 2018

(87) PCT Pub. No.: WO2017/130774
PCT Pub. Date: Aug. 3, 2017

(65) Prior Publication Data
US 2019/0033283 A1 Jan. 31, 2019

(30) Foreign Application Priority Data
Jan. 29, 2016 (JP) .............................. JP2016-015364

(51) Int. Cl.
*G01N 33/02* (2006.01)
*G01N 29/22* (2006.01)
*G01N 29/02* (2006.01)
*G01N 27/12* (2006.01)
*G01N 29/036* (2006.01)

(52) U.S. Cl.
CPC ............. *G01N 33/02* (2013.01); *G01N 27/12* (2013.01); *G01N 29/022* (2013.01); *G01N 29/036* (2013.01); *G01N 29/222* (2013.01); *G01N 2291/014* (2013.01); *G01N 2291/0256* (2013.01); *G01N 2291/0426* (2013.01)

(58) Field of Classification Search
CPC .... G01N 33/02; G01N 29/222; G01N 29/022; G01N 29/036; G01N 27/12; G01N 2291/014; G01N 2291/0256; G01N 2291/0426
USPC ........................................................ 73/23.34
See application file for complete search history.

(56) References Cited

U.S. PATENT DOCUMENTS

2011/0314849 A1\* 12/2011 Park ...................... F25D 29/005
324/439
2013/0015753 A1\* 1/2013 Son ......................... G01N 33/48
312/236

(Continued)

FOREIGN PATENT DOCUMENTS

JP H09-015181 A 1/1997
JP 2002-195971 A 7/2002

(Continued)

*Primary Examiner* — Nimeshkumar D Patel
*Assistant Examiner* — Gedeon M Kidanu
(74) *Attorney, Agent, or Firm* — Studebaker & Brackett PC (57) ABSTRACT

An inspection apparatus includes a container, a connection interface, and a controller. The container stores a specimen. The connection interface is provided inside the container and allows detachable connection of detection units that detect different substances. The controller judges a quality of the specimen stored in the container on the basis of a substance emitted by the specimen and detected by a detection unit connected to the connection interface.

10 Claims, 6 Drawing Sheets

(56) References Cited

U.S. PATENT DOCUMENTS

2013/0288208 A1\* 10/2013 Yamada ............. G09B 19/0092
　　　　　　　　　　　　　　　　　　　　　　　　　434/127
2017/0160005 A1\* 6/2017 Park ...................... F25D 25/005
2018/0274839 A1\* 9/2018 Kim ........................ F25D 29/00

FOREIGN PATENT DOCUMENTS

| JP | 2002-267626 A | 9/2002 |
| JP | 2003-030421 A | 1/2003 |
| JP | 2005-173675 A | 6/2005 |
| JP | 2011-033578 A | 2/2011 |
| JP | 2013-249990 A | 12/2013 |
| JP | 2015-210149 A | 11/2015 |

\* cited by examiner

INSPECTION APPARATUS AND INSPECTION SYSTEM

CROSS-REFERENCE TO RELATED APPLICATION

The present application claims priority to and the benefit of Japanese Patent Application No. 2016-015364 filed Jan. 29, 2016, the entire contents of which are incorporated herein by reference.

TECHNICAL FIELD

The present disclosure relates to an inspection apparatus and an inspection system.

BACKGROUND

A food product management system for managing the deterioration status of a food product is known.

SUMMARY

An inspection apparatus according to an embodiment includes a container, a connection interface, and a controller. The container stores a specimen. The connection interface is provided inside the container and allows detachable connection of detection units that detect different substances. The controller judges a quality of the specimen stored in the container on the basis of a substance emitted by the specimen and detected by a detection unit connected to the connection interface.

An inspection apparatus according to another embodiment includes a container, a plurality of detectors, and a controller. The container includes a plurality of containment chambers each configured to store a specimen. Each of the detectors is disposed in a corresponding containment chamber among the plurality of containment chambers, and each detector is configured to detect a different type of substance emitted by the specimen stored in the corresponding containment chamber. The controller judges a quality of the specimen on the basis of the substance detected by the detector.

An inspection system according to an embodiment includes a detection apparatus and an inspection apparatus. The detection apparatus includes a container, a connection interface, and a communication interface. The container stores a specimen. The connection interface is provided inside the container and allows detachable connection of detection units that detect different substances. The communication interface transmits, to the inspection apparatus, information related to a substance that is emitted by the specimen stored in the container and is detected by a detection unit connected to the connection interface. The inspection apparatus includes a communication interface and a controller. The communication interface receives the information related to the substance from the detection apparatus. The controller judges a quality of the specimen on the basis of the received information related to the substance.

DETAILED DESCRIPTION

An embodiment of the disclosure can improve the usefulness of an inspection apparatus and an inspection system.

Embodiments are described below in detail with reference to the drawings.

First Embodiment

Figure 1:
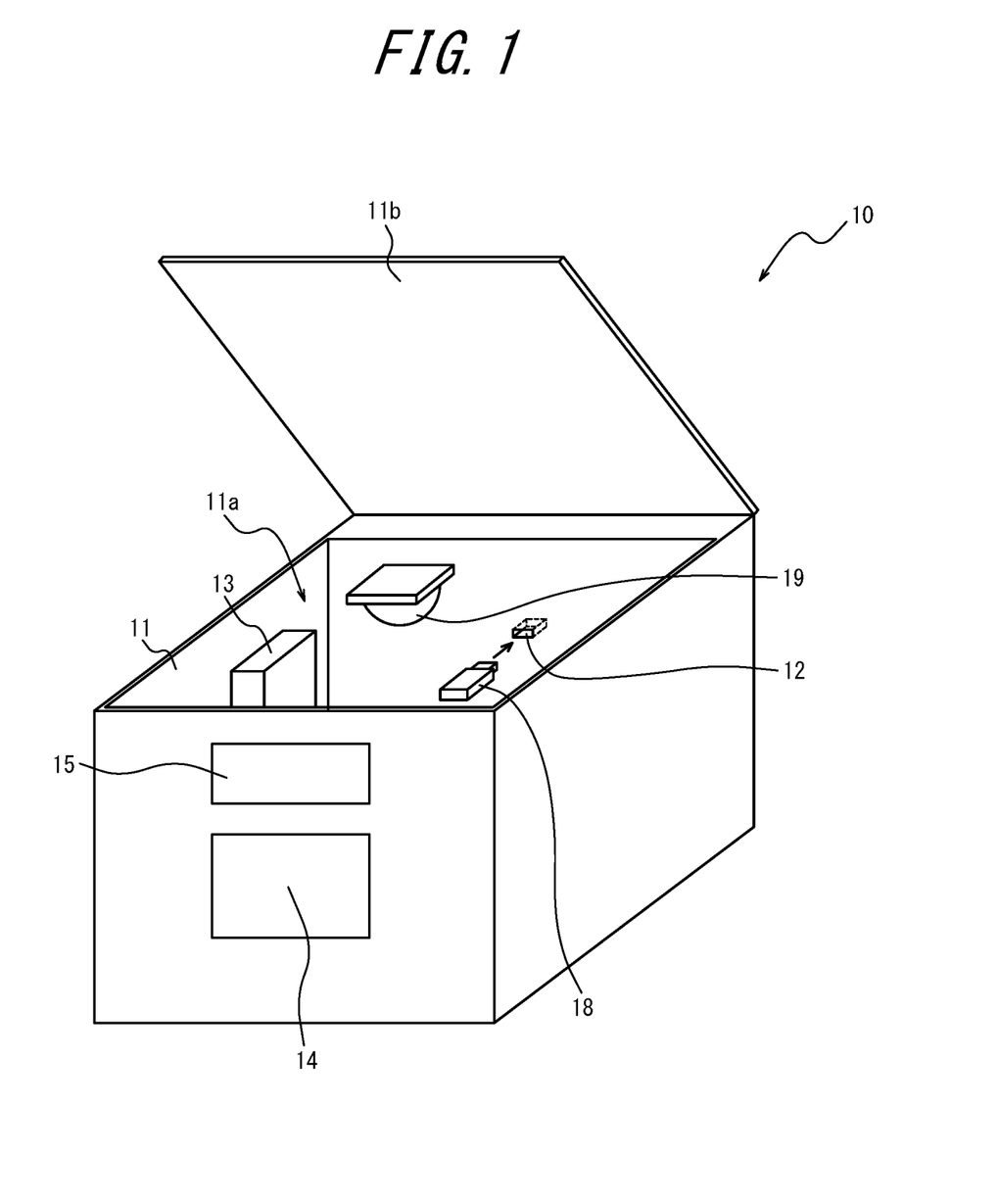
FIG. 1 is an external perspective view schematically illustrating an inspection apparatus according to a first embodiment.

FIG. 1 is an external perspective view schematically illustrating an inspection apparatus according to the first embodiment. An inspection apparatus 10 includes a container 11, a connection interface 12, a deodorizer 13, a notification interface 14, an input interface 15, a controller 16, a memory 17, and a camera 19. Details of the controller 16 and the memory 17 are provided below with reference to the functional block diagram in FIG. 2.

The inspection apparatus 10 executes an inspection process while a detection unit 18 is connected to the connection interface 12 and a specimen is stored in the container 11. In other words, when the inspection apparatus 10 is to execute the inspection process, the user stores the specimen inside the container 11. While the specimen is stored in the container 11, the detection unit 18 connected to the connection interface 12 detects a substance emitted by the specimen. The inspection apparatus 10 judges the quality of the specimen on the basis of the substance detected by the detection unit 18. The inspection apparatus 10 executes the inspection process in this way. The notification interface 14 provides notification of the result of the inspection process. An example of the specimen being a food product is described below in the present embodiment.

The container 11 is, for example, sealable. The container 11 incudes one containment chamber (inspection chamber) 11a, and the specimen is removably stored in the containment chamber 11a. The container 11 includes a pivotable lid 11b. The user of the inspection apparatus 10 opens the lid 11b and stores a food product in the containment chamber 11a. The lid 11b need not be pivotable. It suffices for the lid 11b to adopt a state allowing the user to store a food product in the containment chamber 11a. For example, the container 11 may include a lid 11b that is slidable upward or sideways. The container 11 for example includes a tray, on the bottom of the containment chamber 11a, on which the food product can be placed.

The connection interface 12 is provided in the container 11. The connection interface 12 is configured to allow detachable connection of the detection unit 18, electrically connects the detection unit 18 to the inspection apparatus 10, and holds the detection unit 18 in the container 11. The connection interface 12 is configured as a pin socket, for example. The connection interface 12 is not limited to being a pin socket, however, and may have any structure. In particular, the connection interface 12 allows selective connection of a plurality of types of detection units 18.

The detection unit 18 detects a substance emitted by the food product that is the specimen. The detection unit 18 may, for example, be provided with an odor sensor and detect an odor emitted by the food product. The detection unit 18 may, for example, be provided with a gas sensor and detect a gas emitted by the food product. Specifically, the detection unit 18 includes a sensitive membrane and a transducer. The sensitive membrane adsorbs gas molecules that are the source of the odor, and the transducer converts detection of the gas molecules in the sensitive membrane into an electric signal.

The detection unit 18 may, for example, be provided with a quartz crystal resonator type odor sensor that includes a sensitive membrane, made of an organic thin film, and a quartz crystal resonator. The quartz crystal resonator type odor sensor detects an odor by a change in the resonance frequency of the quartz crystal resonator when gas molecules being adsorbed on the sensitive membrane. The quartz crystal resonator functions as a transducer that converts detection of gas molecules into an electric signal.

The detection unit 18 may, for example, be provided with a semiconductor gas sensor. The semiconductor gas sensor detects the gas concentration by a change in the resistance of a metal oxide semiconductor when gas molecules are adsorbed on the metal oxide semiconductor. The oxide semiconductor functions as a transducer that converts detection of gas molecules into an electric signal. The detection unit 18 may, for example, be provided with an infrared absorption spectrum type gas sensor, an electrochemical gas sensor, a contact combustion type gas sensor, a biosensor, or the like.

To adsorb different types of gas molecules, for example, the detection unit 18 may be provided with a plurality of types of sensitive membranes or metal oxides. The detection unit 18 may be provided with a plurality of quartz crystal resonator type odor sensors, a plurality of semiconductor gas sensors, or a combination of these sensors. The detection unit 18 transmits the electric signal converted by the transducer to a controller, provided in the inspection apparatus 10, as odor-related information. The controller provided in the inspection apparatus 10 is described below in detail.

The plurality of types of detection units 18 are provided with different odor sensors in accordance with the types of odors to be detected. In other words, the plurality of detection units 18 detect different substances. In accordance with the particular quality of the food product to be inspected by the inspection apparatus 10 (the quality to be judged), the user can select a detection unit 18, from among the plurality of types of detection units 18, that is capable of detecting information of an odor related to the quality of the food product to be inspected. The user can then connect the detection unit 18 to the connection interface 12 and cause the inspection apparatus 10 to execute the inspection process.

The quality of the food product may, for example, refer to whether the food product is spoiled. In this case, the user connects a detection unit 18 provided with an odor sensor capable of detecting an odor serving as an index of the degree of spoiling of the food product to the connection interface 12 and causes the inspection apparatus 10 to execute the inspection process.

The quality of the food product may, for example, refer to whether the food product is ripe. In this case, the user connects a detection unit 18 provided with an odor sensor capable of detecting an odor serving as an index of whether the food product is ripe to the connection interface 12 and causes the inspection apparatus 10 to execute the inspection process.

The quality of the food product may, for example, refer to the degree of aging of the food product. In this case, the user connects a detection unit 18 provided with an odor sensor capable of detecting an odor serving as an index of the degree of aging of the food product to the connection interface 12 and causes the inspection apparatus 10 to execute the inspection process.

The quality of the food product may, for example, refer to the freshness of the food product. In this case, the user connects a detection unit 18 provided with an odor sensor capable of detecting an odor serving as an index of the freshness of the food product to the connection interface 12 and causes the inspection apparatus 10 to execute the inspection process.

The quality of the food product may, for example, refer to the production area of the food product. In this case, the user connects a detection unit 18 provided with an odor sensor capable of detecting an odor for identifying the production area of the food product to the connection interface 12 and causes the inspection apparatus 10 to execute the inspection process.

The quality of the food product may, for example, refer to the extent of residual pesticide in the food product. In this case, the user connects a detection unit 18 provided with an odor sensor capable of detecting an odor serving as an index of the extent of residual pesticide in the food product to the connection interface 12 and causes the inspection apparatus 10 to execute the inspection process.

In accordance with a particular quality of the food product, the user in the above-described example connects a detection unit 18 capable of detecting information of an odor related to the quality of the food product to be inspected to the connection interface 12. The method of determining the detection unit 18 to connect to the connection interface 12, however, is not limited to the quality of the food product. For example, when a plurality of detection units 18 correspond to various types of food, then in accordance with the particular quality of the food product to be inspected and the type of food, the user can connect a detection unit 18 capable of detecting information of an odor related to the quality of the food to be inspected to the connection interface 12 and cause the inspection apparatus 10 to execute the inspection process. The types of food may, for example, be meat, fish, vegetables, fruits, milk products, and the like.

The quality of the food product is not limited to the above-described examples and may be any other property or quality related to the food product.

The deodorizer 13 performs a deodorization process on the inside of the container 11. For example, the deodorizer 13 is configured by a degassing apparatus, a deodorizing apparatus, or the like. When the deodorizer 13 is configured to include a degassing apparatus, the deodorizer 13 deodorizes the container 11 by expelling (degassing) gas molecules from inside the container 11 to the outside. When the deodorizer 13 is configured to include an ozone deodorizing apparatus, the deodorizer 13 discharges ozone into the container 11. The discharged ozone decomposes gas molecules to deodorize the inside of the container 11. When the deodorizer 13 is configured to include an oxygen cluster deodorizing apparatus, the deodorizer 13 ionizes the oxygen molecules inside the container 11. The ionized oxygen molecules (oxygen cluster ions) subject gas molecules inside the container 11 to ion decomposition to deodorize the inside of the container 11.

The deodorizer 13 is, for example, located inside the container 11. In FIG. 1, the deodorizer 13 is located on an inner side wall of the container 11.

The notification interface 14 provides notification of the result of the inspection process by the inspection apparatus 10. The notification interface 14 can, for example, provide notification by a visual method using image, character, or color display, light emission, or the like; an auditory method using audio or the like; or a combination of these methods. To provide notification with a visual method, the notification interface 14 may be a display device that provides notification by displaying images or characters. The notification interface 14 may, for example, provide notification by emitting light with an LED or the like. To provide notification with an auditory method, the notification interface 14 may be a speaker or other such sound generating device that provides notification by outputting an alarm, audio guidance, or the like. The notification interface 14 is not limited to providing notification by a visual or auditory method. Any method recognizable by the subject may be adopted. For example, the notification interface 14 may provide notification with a vibration pattern or the like.

In the example in FIG. 1, the notification interface 14 is a display device located outside of the container 11 and provides notification of the result of the inspection process with images, characters, color, or the like.

The input interface 15 accepts operation input from the user and may be configured by operation buttons (operation keys), for example. The input interface 15 may be configured by a touchscreen and accept touch operation input from the user to an input region, displayed on a portion of the display device that is the notification interface 14, for accepting operation input. The user may, for example, instruct the inspection apparatus 10 to start inspection by operating the input interface 15 (by an inspection operation). The user may, for example, input the type of food product that is the specimen by operating the input interface 15.

The inspection apparatus 10 may include the camera 19. On the basis of control by the inspection apparatus 10, the camera 19 captures an image of the specimen. Information related to the imaged specimen is transmitted to the below-described controller along with the odor-related information.

Figure 2:
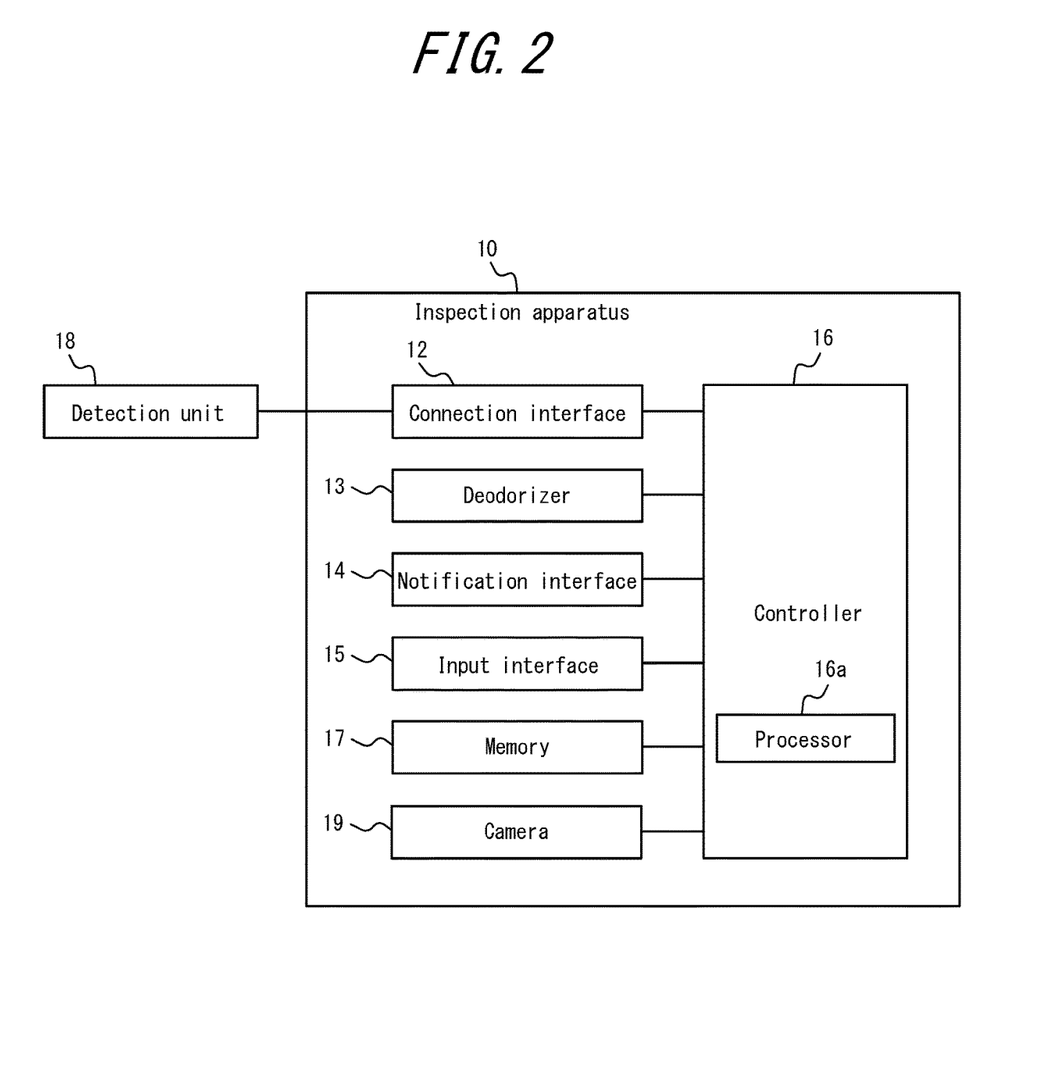
FIG. 2 is a functional block diagram illustrating the schematic configuration of the inspection apparatus in FIG. 1.

FIG. 2 is a functional block diagram illustrating the schematic configuration of the inspection apparatus 10 in FIG. 1. FIG. 2 is a functional block diagram illustrating a state in which the detection unit 18 is connected to the connection interface 12. As illustrated in FIG. 2, the inspection apparatus 10 includes the connection interface 12, the deodorizer 13, the notification interface 14, the input interface 15, the controller 16, and the memory 17.

The controller 16 is a processor that controls and manages the inspection apparatus 10 overall, starting with the functional blocks of the inspection apparatus 10. The controller 16 is a processor, such as a central processing unit (CPU), that executes a program prescribing control procedures. Such a program is, for example, stored in the memory 17 or on an external storage medium.

To provide control and processing capability for executing various functions, as described below in greater detail, the inspection apparatus 10 is provided with the controller 16, which includes one or more processors 16a.

In various embodiments, the one or more processors 16a may be implemented as a single integrated circuit or as a plurality of communicatively connected integrated circuits and/or discrete circuits. The one or more processors 16a can be implemented with a variety of known techniques.

In an embodiment, the processor 16a includes one or more circuits or units configured to execute one or more data calculation procedures or processes by executing instructions stored in related memory, for example. In another embodiment, the processor 16a may be firmware (such as discrete logic components) configured to execute one or more data calculation procedures or processes.

In various embodiments, the processor 16a may include one or more processors, controllers, microprocessors, microcontrollers, application specific integrated circuits (ASIC), digital signal processors, programmable logic devices, field programmable gate arrays, any combination of these devices or structures, or a combination of other known devices and structures, to execute the below-described functions.

The controller 16 executes the inspection process using the inspection apparatus 10 by controlling the entire inspection apparatus 10. For example, on the basis of a predetermined operation (inspection operation) input by the user of the inspection apparatus 10 to the input interface 15, the controller 16 activates the detection unit 18 connected through the connection interface 12. The detection unit 18 activated by the controller 16 starts to detect an odor emitted by the food product. The controller 16 acquires information related to the odor detected by the detection unit 18 from the detection unit 18.

The controller 16 judges the quality of the food product on the basis of the odor detected by the detection unit 18. In other words, the controller 16 judges the quality of the food product on the basis of the odor-related information acquired from the detection unit. For example, the detection unit 18 may include a plurality of different odor sensors that adsorb gas molecules such as ethylene, ammonia, alcohol, aldehyde, and sulfur gas molecules. The controller 16 may judge the quality of the food product on the basis of a plurality of signals detected by the plurality of odor sensors. The components of gas molecules that are the source of the odor emitted by a food product, the ratio of the components, and the like differ depending on the food product and the quality of the food product. Therefore, the controller 16 judges the quality of a food product on the basis of odor-related information, i.e. the components of gas molecules that are the source of the odor, the ratio of the components, and the like. The controller 16 may, for example, judge the quality of the food product on the basis of the outputs of a plurality of odor sensors and the ratio of the outputs. The controller 16 may, for example, judge the quality of the food product on the basis of features (output value, time constant, or the like) of the response of a plurality of odor sensors. The detector 12 may, for example, include a plurality of ethylene, alcohol, sulfur, and ammonia type odor sensors. When judging the quality of a vegetable, for example, the controller 16 may judge that the quality has deteriorated when the outputs of the alcohol, sulfur, and ammonia type odor sensors among the plurality of odor sensor outputs increase to a predetermined value or higher. The controller 16 refers to information (data), stored in the memory 17, associating the odor emitted by a food product and the quality of the food product to judge the quality of the food product. Here, the quality of a food product refers to the properties or qualities of the food product.

The detection unit 18, which is provided with an odor sensor capable of detecting an odor related to a particular quality, is connected to the connection interface 12. Odor-related information that the detection unit 18 can acquire with the odor sensor is therefore transmitted to the controller 16. Consequently, the controller 16 judges the quality of the food product corresponding to the odor on the basis of the particular odor-related information acquirable by the odor sensor of the detection unit 18.

For example, when the detection unit 18 is provided with an odor sensor capable of detecting an odor serving as an index of the degree of spoiling of the food product, odor-related information that serves as an index of the degree of spoiling of the food product is transmitted to the controller 16. As the quality of the food product, the controller 16 in this case judges whether the food product is spoiled on the basis of the acquired odor-related information.

Similarly, when the detection unit 18 is provided with an odor sensor capable of detecting an odor serving as an index of whether the food product is ripe, then as the quality of the food product, the controller 16 judges whether the food product is ripe on the basis of the acquired odor-related information. When the detection unit 18 is provided with an odor sensor capable of detecting an odor that indicates the degree of aging of the food product, then as the quality of the food product, the controller 16 judges the degree of aging of the food product on the basis of the acquired odor-related information. When the detection unit 18 is provided with an odor sensor capable of detecting an odor serving as an index of the freshness of the food product, then as the quality of the food product, the controller 16 judges the freshness of the food product on the basis of the acquired odor-related information. When the detection unit 18 is provided with an odor sensor capable of detecting an odor for identifying the production area of the food product, then as the quality of the food product, the controller 16 judges the production area of the food product on the basis of the acquired odor-related information. When the detection unit 18 is provided with an odor sensor capable of detecting an odor serving as an index of the extent of residual pesticide in the food product, then as the quality of the food product, the controller 16 judges the extent of residual pesticide in the food product on the basis of the acquired odor-related information.

A plurality of detection units 18 may correspond to various types of food. The user selects a detection unit 18 in accordance with the type of food, connects the detection unit 18 to the connection interface 12, and causes the inspection apparatus 10 to execute the inspection process. The types of food may, for example, be meat, fish, vegetables, fruits, milk products, and the like. When the user connects a detection unit 18 for meat to the connection interface 12, for example, the controller 16 judges the quality level until spoiling on the basis of the degree of aging of the meat. When the user connects a detection unit 18 for fruit to the connection interface 12, for example, the controller 16 judges whether the fruit is ripe as the quality of the fruit.

The quality of the food product is not limited to the above-described examples and may be any other property or quality related to the food product. The controller 16 may judge the odor using a statistical method, such as principal component analysis, or using a neural network. The controller 16 may generate data by performing a learning process in advance to extract the features of the response of a plurality of odor sensors for each quality of a food product. The controller 16 may store the data after learning in the memory 17. The controller 16 may then judge the quality of the food product on the basis of the degree of matching between the data after learning stored in the memory 17 and the data detected by the detector 12. Based on newly detected data, the controller 16 may update the data after learning stored in the memory 17.

The controller 16 may judge the quality of the specimen on the basis of the odor-related information acquired by the detection unit 18 and information related to the specimen imaged by the camera 19. The controller 16 may, for example, infer the type of specimen on the basis of the information related to the specimen imaged by the camera 19. A plurality of sets of information (data) associating the odor emitted by a specimen and the quality of the specimen are stored in the memory 17 for each type of specimen. The controller 16 may refer to the information (data) corresponding to the inferred type of specimen to judge the quality of the specimen.

The controller 16 may judge the quality of the specimen on the basis of the odor-related information and the specimen type input by operation of the input interface 15. The controller 16 may refer to the information (data) corresponding to the input type of specimen to judge the quality of the specimen.

The controller 16 provides notification of information related to the judged quality of the food product through the notification interface 14 as the result of the inspection process. As described above, the notification method may be any method recognizable by the subject. When the notification interface 14 is a display device, as illustrated in FIG. 1, the controller 16 provides notification by display of images, characters, or colors on the display device.

The controller 16 stores information related to the judged quality of the food product in the memory 17 as history data, for example.

Before or after the detection unit 18 detects an odor, the controller 16 may execute a refresh process to refresh the inside of the container 11. The refresh process is a process to reduce factors that can cause detection errors during odor detection by the detection unit 18. The controller 16 may, for example, execute the refresh process by activating the deodorizer 13 to degas or deodorize the inside of the container 11. The controller 16 may, for example, execute the refresh process by resetting the detection unit 18. By being reset, the detection unit 18 can use the internal state of the container 11 at the time of resetting as a reference to detect a change in the odor inside the container 11 due to an odor emitted by a food product newly stored in the container 11, for example.

The controller 16 can improve the accuracy of odor detection by executing the refresh process before odor detection. The controller 16 can improve the accuracy of odor detection during the next detection process by executing the refresh process after odor detection.

The memory 17 may be configured with a semiconductor memory, a magnetic memory, or the like. The memory 17 stores a variety of information, programs for causing the inspection apparatus 10 to operate, and the like and also functions as a working memory. For example, the memory 17 stores information (data) associating the odor emitted by a food product and the quality of the food product. The memory 17 may, for example, store the result of the detection process by the inspection apparatus 10 as history data.

The camera 19 captures an image of the food product stored in the container 11. The camera 19 transmits information related to the imaged food product to the controller 16. The inspection apparatus 10 may further include an optical emitter to produce a flash when the camera 19 captures an image.

Figure 3:
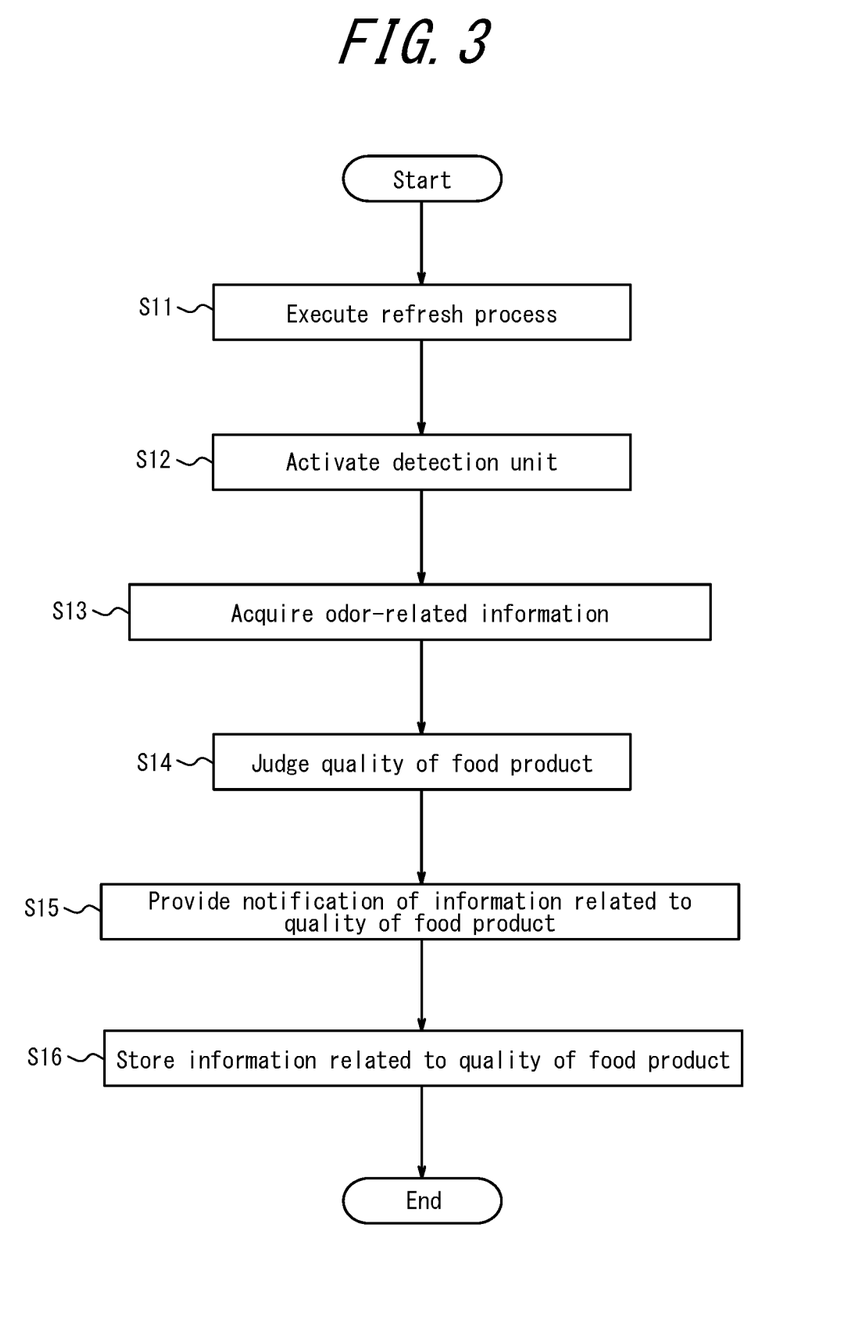
FIG. 3 is a flowchart illustrating an example of an inspection process executed by the controller in FIG. 2.

Next, with reference to the flowchart in FIG. 3, an example of the process executed by the controller 16 when the inspection apparatus 10 executes the inspection process is described. Here, the controller 16 is described as executing the refresh process before the odor detection process by the detection unit 18.

To inspect the quality of the food product using the inspection apparatus 10, the user first opens the lid 11b of the inspection apparatus 10 and connects the type of detection unit 18 corresponding to the quality to be detected to the connection interface 12. Next, the user stores the food product to be judged in the container 11. The user then closes the lid 11b to seal the container 11. Subsequently, the user instructs the inspection apparatus 10 to start the inspection process by inputting an operation (inspection operation) to the input interface 15.

Once the user inputs the predetermined operation (inspection operation), the controller 16 starts the process in FIG. 3.

The controller 16 executes the refresh process by, for example, activating the deodorizer 13 (step S11).

The controller 16 activates the detection unit 18 (step S12). By being activated by the controller 16, the detection unit 18 starts to detect an odor emitted by the food product stored in the container 11.

From the detection unit 18, the controller 16 acquires the odor-related information obtained by the detection unit 18 (step S13).

On the basis of the acquired odor-related information, the controller 16 refers to the data stored in the memory 17 to judge the quality of the food product (step S14).

The controller 16 provides notification of information related to the quality of the food product judged in step S14 through the notification interface 14 (step S15). The user can learn the quality of the food product by the notification from the notification interface 14.

The controller 16 stores the information related to the quality of the food product judged in step S14 in the memory 17 (step S16).

Before judging the quality of the food product in step S14, the controller 16 may capture an image of the specimen using the camera 19 and infer the type of food product on the basis of information related to the imaged specimen. In this case, the controller 16 may refer to information (data) corresponding to the inferred type of food product to judge the quality of the food product.

In accordance with an inspection operation, the inspection apparatus 10 according to the present embodiment thus uses the detection unit 18 connected to the connection interface 12 to detect an odor emitted by a food product stored in the container 11. On the basis of the detected odor, the inspection apparatus 10 judges the quality of the food product. Therefore, when the user wishes to learn the quality of a food product, the user can do so immediately by placing the food product in the container 11 and causing the inspection apparatus 10 to execute the inspection process. Furthermore, when the user wishes to inspect a different quality, the user switches the detection unit 18 connected to the connection interface 12 with the type of detection unit 18 corresponding to the quality to be judged and then causes the inspection apparatus 10 to execute the inspection process. By thus appropriately selecting the detection unit 18 to connect to the connection interface 12, the user can use the inspection apparatus 10 to inspect a variety of qualities of a food product. Accordingly, the inspection apparatus 10 allows the quality of a food product to be inspected in accordance with user need, thereby improving usefulness as compared to known apparatuses.

The inspection apparatus 10 according to the present embodiment allows one inspection apparatus 10 to inspect the quality of a plurality of food products by switching of the food product stored in the container 11.

Second Embodiment

Figure 4:
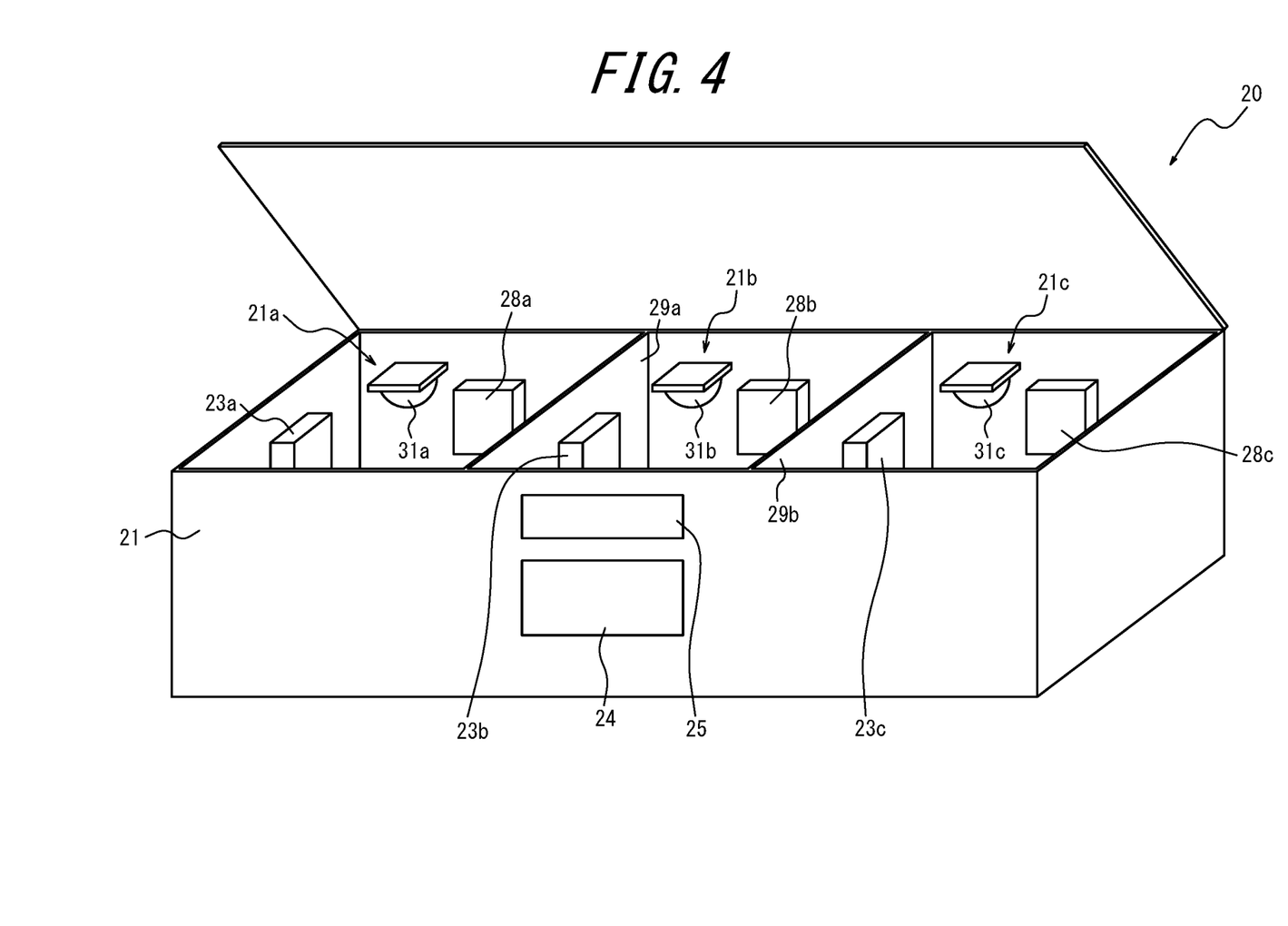
FIG. 4 is an external perspective view schematically illustrating an inspection apparatus according to a second embodiment.

FIG. 4 is an external perspective view schematically illustrating an inspection apparatus according to a second embodiment. In the second embodiment, a container 21 of an inspection apparatus 20 includes a plurality of containment chambers. In the present embodiment, the inspection apparatus 20 is described as including three containment chambers 21a, 21b, and 21c, but the number of containment chambers is not limited to three. It suffices for the inspection apparatus 20 to include two or more containment chambers. The containment chambers 21a and 21b are partitioned by a partition 29a. The containment chambers 21b and 21c are partitioned by a partition 29b. The containment chambers 21a, 21b, and 21c are each sealable. A tray on which a food product can be placed is located at the bottom of each of the containment chambers 21a, 21b, and 21c. The following describes the differences from the first embodiment, omitting a description of common features.

The inspection apparatus 20 is provided with a detector 28a, deodorizer 23a, and camera 31a in the containment chamber 21a; a detector 28b, deodorizer 23b, and camera 31b in the containment chamber 21b; and a detector 28c, deodorizer 23c, and camera 31c in the containment chamber 21c. The detectors 28a, 28b, and 28c and the cameras 31a, 31b, and 31c have the same functions as the detection unit 18 and the camera 19 in the first embodiment. Specifically, the detectors 28a, 28b, and 28c detect a substance emitted by the food products that are the specimens stored in the respective containment chambers 21a, 21b, and 21c. Here, the detectors 28a, 28b, and 28c are provided with different odor sensors and detect different qualities.

The function of the deodorizers 23a, 23b, and 23c is the same as that of the deodorizer 13 in the first embodiment. In other words, the deodorizers 23a, 23b, and 23c perform a deodorization process on the inside of the respective containment chambers 21a, 21b, and 21c.

The inspection apparatus 20 is further provided with a notification interface 24 and an input interface 25. Since the functions of the notification interface 24 and the input interface 25 are the same as those of the notification interface 14 and the input interface 15 in the first embodiment, a description thereof is omitted.

To perform an inspection process using the inspection apparatus 20 of the present embodiment, the user stores a food product in one of the containment chambers 21a, 21b, and 21c in accordance with the quality to be judged and causes the inspection apparatus 20 to execute the inspection process.

Suppose, for example, that the detector 28a of the containment chamber 21a is provided with a sensor capable of detecting an odor serving as an index of the degree of spoiling of the food product. Further suppose that the detector 28b of the containment chamber 21b is provided with an odor sensor capable of detecting an odor serving as an index of whether the food product is ripe. Also suppose that the detector 28c of the containment chamber 21c is provided with a sensor capable of detecting an odor serving as an index of the degree of aging of the food product. When, for example, the user wishes to know whether the food product is spoiled, the user stores the food product in the containment chamber 21a and starts the inspection process. Similarly, when wishing to know whether the food product is ripe, the user stores the food product in the containment chamber 21b and starts the inspection process. When wishing to know the degree of aging of the food product, the user stores the food product in the containment chamber 21c and starts the inspection process.

For example, the containment chambers 21a, 21b, and 21c may correspond to different types of food products. Suppose that the detector 28a of the containment chamber 21a is provided with a sensor capable of detecting an odor serving as an index of the degree of spoiling of fish. Further suppose that the detector 28b of the containment chamber 21b is provided with an odor sensor capable of detecting an odor serving as an index of whether fruit is ripe. Also suppose that the detector 28c of the containment chamber 21c is provided with a sensor capable of detecting an odor serving as an index of the degree of aging of meat. When, for example, the user wishes to know the quality of fish, the user stores the food product in the containment chamber 21a and starts the inspection process. Similarly, when wishing to know the quality of fruit, the user stores the food product in the containment chamber 21b and starts the inspection process. When wishing to know the quality of meat, the user stores the food product in the containment chamber 21c and starts the inspection process.

In the inspection apparatus 20 according to the present embodiment, the input interface 25 may, for example, prompt the user to indicate the containment chamber in which to execute the odor detection process from among the three containment chambers 21a, 21b, and 21c. In this way, the inspection apparatus 20 can activate the detector inside the containment chamber corresponding to the operation input by the user and execute the odor detection process. The inspection apparatus 20 may, for example, automatically determine the containment chamber in which the food product is stored and activate the detector in the determined containment chamber to execute the odor detection process.

Figure 5:
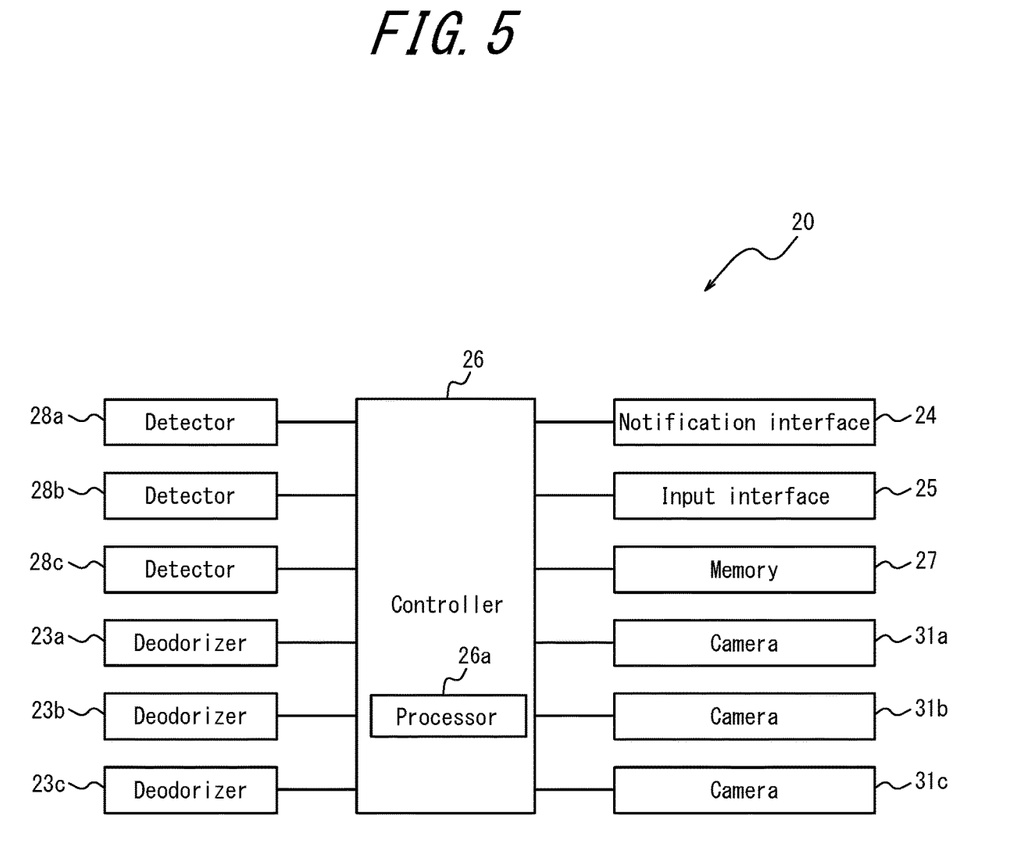
FIG. 5 is a functional block diagram illustrating the schematic configuration of the inspection apparatus in FIG. 4.

FIG. 5 is a functional block diagram illustrating the schematic configuration of the inspection apparatus 20 in FIG. 4. As illustrated in FIG. 5, the inspection apparatus 20 includes the detectors 28a, 28b, and 28c, the deodorizers 23a, 23b, and 23c, the notification interface 24, the input interface 25, the controller 26, and the memory 27.

The controller 26 controls and manages the inspection apparatus 20 overall, starting with the functional blocks of the inspection apparatus 20. To provide control and processing capability for executing various functions, the controller 26 may include at least one processor 26a. The memory 27 may be configured with a semiconductor memory, a magnetic memory, or the like. The memory 27 stores a variety of information, programs for causing the inspection apparatus 20 to operate, and the like and also functions as a working memory. The functions of the controller 26 and the memory 27 are similar to those of the controller 16 and the memory 17 in the first embodiment. In other words, on the basis of operation input from the user to the input interface 25, the controller 26 executes an odor detection process by the detector 28a, 28b, or 28c and judges the quality of the food product on the basis of the odor detected by the detector 28a, 28b, or 28c. The controller 26 may judge the quality of the specimen on the basis of the odor-related information acquired by the detector 28a, 28b, or 28c and information related to the specimen imaged by the camera 31a, 31b, or 31b.

In this way, the inspection apparatus 20 according to the present embodiment detects odors emitted by the food products stored in the containment chambers 21a, 21b, and 21c using the respective detectors 28a, 28b, 28c and judges the quality of the food products on the basis of the detected odors. Therefore, when the user wishes to learn the quality of a food product, the user can do so immediately by placing the food product in the containment chamber 21a, 21b, or 21c and causing the inspection apparatus 20 to execute the inspection process. Accordingly, the inspection apparatus 20 allows the quality of a food product to be inspected in accordance with user need, thereby improving usefulness as compared to known apparatuses. The user can use the inspection apparatus 20 to inspect a desired quality of a food product by selecting, in accordance with the quality to be judged or the type of food product, one of the containment chambers 21a, 21b, and 21c for storing a food product.

The inspection apparatus 10 in the first embodiment has been described as including the connection interface 12, to which the detection unit 18 is connected, and the controller 16 that judges the quality of a food product. The connection interface 12, to which the detection unit 18 is connected, and the functional unit that judges the quality may, however, be provided in separate apparatuses capable of communicating with each other. The case of the connection interface 12, to which the detection unit 18 is connected, and the functional unit that judges the quality being provided in separate apparatuses is described as a third embodiment with reference to FIG. 6.

Third Embodiment

Figure 6:
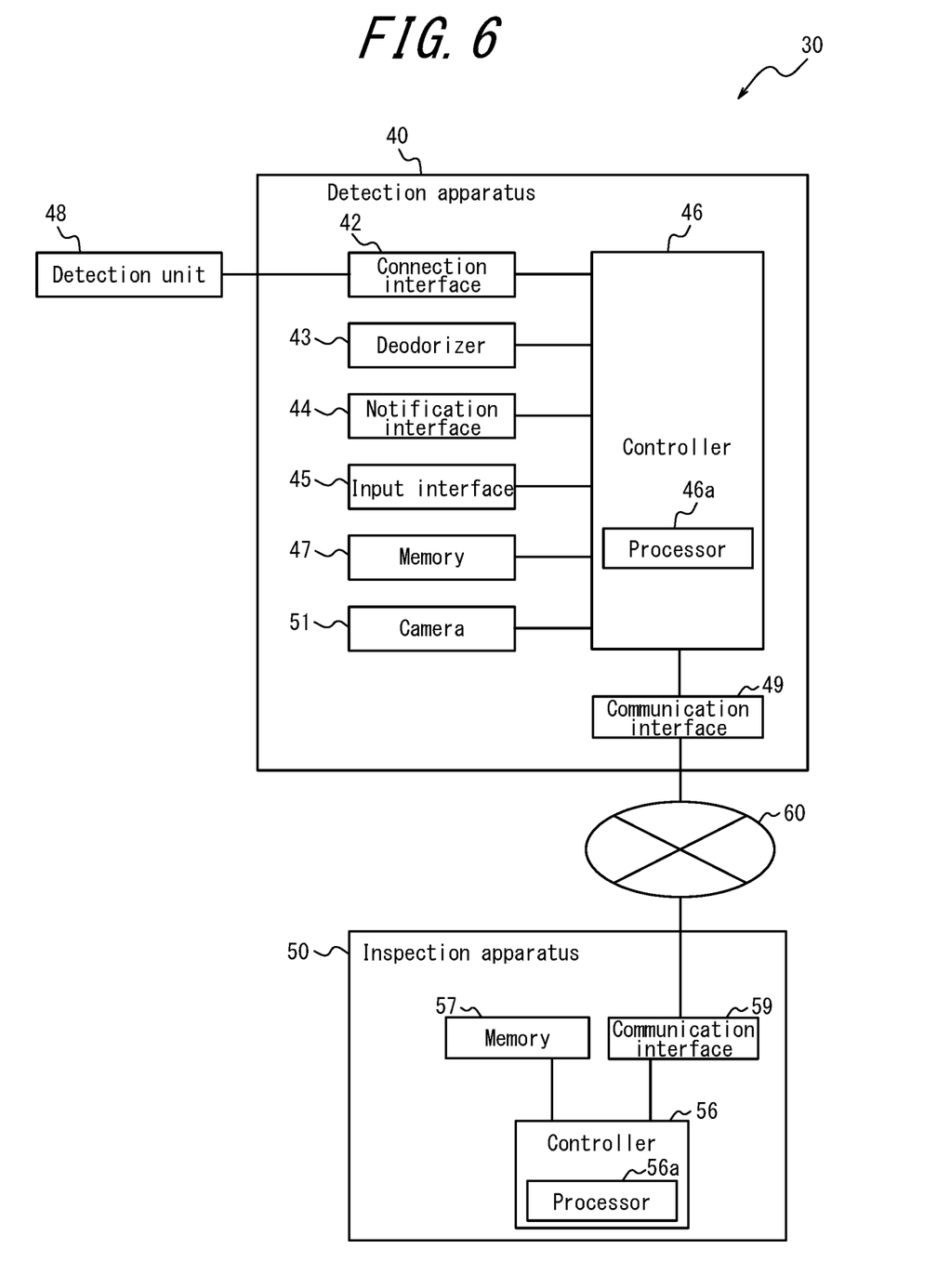
FIG. 6 is a functional block diagram illustrating the schematic configuration of an inspection system according to a third embodiment.

FIG. 6 is a functional block diagram illustrating the schematic configuration of an inspection system according to the third embodiment. As illustrated in FIG. 6, the inspection system 30 includes a detection apparatus 40 and an inspection apparatus 50. The detection apparatus 40 and the inspection apparatus 50 connect to allow communication therebetween over a network 60, such as an Internet connection, a wide area network (WAN), or a local area network (LAN).

The detection apparatus 40 may, for example, be configured as a container that includes a lid, as in the inspection apparatus 10 illustrated in FIG. 1. The detection apparatus 40 includes a connection interface 42, a deodorizer 43, a notification interface 44, an input interface 45, a controller 46, a memory 47, a communication interface 49, and a camera 51. The connection interface 42 is configured to allow detachable connection of a detection unit 48 that has the same functions as the detection unit 18. The functions of the deodorizer 43, notification interface 44, input interface 45, and camera 51 are respectively similar to the functions of the deodorizer 13, notification interface 14, input interface 15, and camera 19 described with reference to FIG. 1. Hence, a description thereof is omitted.

The controller 46 controls and manages the detection apparatus 40 overall, starting with the functional blocks of the detection apparatus 40. To provide control and processing capability for executing various functions, the controller 46 may include at least one processor 46a. The controller 46 does not judge the quality of a food product, unlike the controller 46 described with reference to FIG. 2. The controller 46 transmits odor-related information acquired from the detection unit 18 to the inspection apparatus 50 through the communication interface 49. The controller 46 may also transmit information, related to the imaged specimen, acquired from the camera 51 to the inspection apparatus 50 through the communication interface 49.

From the inspection apparatus 50, the controller 46 acquires information related to the quality of a food product judged by the inspection apparatus 50. Upon acquiring the information related to the quality of the food product, the controller 46 provides notification of the information related to the quality of the food product through the notification interface 44. The controller 46 stores the information related to the quality of the food product in the memory 47.

The communication interface 49 exchanges a variety of information with the inspection apparatus 50 by wired or wireless communication. For example, the communication interface 49 transmits the odor-related information to the inspection apparatus 50. For example, the communication interface 49 receives the information related to the quality of the food product from the inspection apparatus 50. The odor-related information may, for example, be transmitted from the detection apparatus 40 to the inspection apparatus 50 each time the controller 46 acquires the odor-related information from the detection unit 48. The odor-related information may, for example, be transmitted from the detection apparatus 40 to the inspection apparatus 50 when the user provides predetermined operation input to the detection apparatus 40. The communication interface 49 may, for example, receive the information related to the imaged specimen from the detection apparatus 40.

The inspection apparatus 50 may, for example, be configured as a server. The inspection apparatus 50 includes a controller 56, a memory 57, and a communication interface 59.

The controller 56 controls and manages the inspection apparatus 50 overall, starting with the functional blocks of the inspection apparatus 50. To provide control and processing capability for executing various functions, the controller 56 may include at least one processor 56a. The controller 56 judges the quality of the food product on the basis of the odor-related information received by the communication interface 59 from the detection apparatus 40. At this time, the controller 56 refers to information (data), stored in the memory 57, associating the odor emitted by a food product and the quality of the food product to judge the quality of the food product. The controller 56 transmits information related to the judged quality of the food product to the detection apparatus 40 through the communication interface 59. The controller 56 may judge the quality of the food product after inferring the type of food product on the basis of the information related to the imaged specimen.

By communicating with the detection apparatus 40 over the network 60, the communication interface 59 transmits and receives a variety of information. For example, the communication interface 59 receives the odor-related information from the detection apparatus 40. For example, the communication interface 59 transmits the information related to the quality of the food product to the detection apparatus 40.

In the inspection system 30 illustrated as an example in FIG. 6, the user can cause the detection apparatus 40 to detect odor-related information by using the detection apparatus 40 with the same method as the method of using the inspection apparatus 10 described with reference to FIGS. 1 and 2. The user can also learn the quality of the food product by the notification from the notification interface 44 of the detection apparatus 40.

Since the inspection apparatus 50 that is a server judges the quality of the food product, the data in the memory 57 referred to by the controller 56 of the inspection apparatus 50 can be updated as necessary in the inspection system 30. In other words, the quality of the food product is judged on the basis of updated data in the inspection system 30.

The inspection apparatus and the inspection system are not limited to the above embodiments, and a variety of modifications and changes may be made. For example, the functions and the like included in the components, steps, and the like may be reordered in any logically consistent way. Furthermore, components, steps, and the like may be combined into one or divided.

For example, the detection unit 18 has been described in the first embodiment as being an odor sensor that detects an odor emitted by a food product. The detection unit 18 may, however, be a sensor other than an odor sensor. For example, the detection unit 18 may be a gas sensor that detects odorless gas molecules emitted by the specimen.

For example, the connection interface 12 has been described in the first embodiment as electrically connecting the detection unit 18 to the inspection apparatus 10 and holding the detection unit 18 in the container 11. The connection interface 12 is not, however, limited to this configuration. For example, the detection unit 18 may be constituted by a detection unit body and wiring connected to the detection unit body, and the connection interface 12 may electrically connect the detection unit 18 to the inspection apparatus 10 via this wiring. In this case, the detection unit body is stored (arranged) at a predetermined position inside the container 21, for example.

The invention claimed is:

1. An inspection apparatus comprising:
   a container configured to store a specimen;
   a camera configured to capture an image of the specimen;
   a connection interface, provided inside the container, configured to allow detachable connection of detection units that detect different substances, selectively by type of the substances; and
   a controller configured to infer a type of the specimen on the basis of information related to the specimen imaged by the camera, and to judge in accordance with the type of the specimen a quality of the specimen stored in the container on the basis of a gaseous substance emitted by the specimen and detected by a detection unit connected to the connection interface,
   wherein the connection interface is electrically connected to the controller.

2. The inspection apparatus of claim 1, wherein a detection unit of a type corresponding to a quality to be judged is connected to the connection interface, and the controller is configured to acquire information related to the gaseous substance detected by the detection unit and to judge the quality of the specimen on the basis of the acquired information.

3. The inspection apparatus of claim 1, wherein the inspection apparatus executes a refresh process of the container before the detection unit detects the gaseous substance.

4. The inspection apparatus of claim 1, further comprising:
   a memory configured to store information associating the gaseous substance emitted by the specimen and the quality of the specimen; wherein
   the controller refers to the information stored in the memory to judge the quality of the specimen stored in the container.

5. The inspection apparatus of claim 1, further comprising a notification interface configured to provide notification of information related to the quality judged by the controller.

6. The inspection apparatus of claim 1, wherein
   the specimen is a food product; and
   as the quality of the food product, the controller is configured to judge, in accordance with a type of the detection unit, at least one of whether the food product is spoiled, whether the food product is ripe, a degree of aging of the food product, a freshness of the food product, a production area of the food product, and an extent of residual pesticide in the food product.

7. The inspection apparatus of claim 1, wherein the inspection apparatus executes a refresh process of the container after the detection unit detects the gaseous substance.

8. The inspection apparatus of claim 3, wherein the refresh process includes at least one of degassing the container, deodorizing the container, and resetting the detection unit.

9. An inspection apparatus comprising:
a container comprising a plurality of containment chambers each configured to store a specimen;
a camera configured to capture an image of the specimen;
a plurality of detectors, each detector being disposed in a corresponding containment chamber among the plurality of containment chambers and each detector being configured to detect a different type of gaseous substance emitted by the specimen stored in the corresponding containment chamber, selectively by type of the substance; and
a controller configured to infer a type of the specimen on the basis of information related to the specimen imaged by the camera, and to judge in accordance with the type of the specimen a quality of the specimen on the basis of the gaseous substance detected by the detector,
wherein the plurality of detectors are electrically connected to the controller.

10. An inspection system comprising:
a detection apparatus; and
an inspection apparatus; wherein
the detection apparatus comprises a container configured to store a specimen, a camera configured to capture an image of the specimen, a connection interface, provided inside the container, configured to allow detachable connection of detection units that detect different substances, selectively by type of the substances, and a communication interface configured to transmit, to the inspection apparatus, information related to a gaseous substance that is emitted by the specimen stored in the container and is detected by a detection unit connected to the connection interface;
the inspection apparatus comprises a communication interface configured to receive the information related to the gaseous substance from the detection apparatus and a controller configured to infer a type of the specimen on the basis of information related to the specimen imaged by the camera, and to judge in accordance with the type of the specimen a quality of the specimen on the basis of the received information related to the gaseous substance, and
the connection interface is electrically connected to the controller.

* * * * *